(12) United States Patent
Levy

(10) Patent No.: US 7,357,868 B2
(45) Date of Patent: *Apr. 15, 2008

(54) NANOCRYSTAL-CONTAINING FILTRATION MEDIA

(75) Inventor: Ehud Levy, Rosewell, GA (US)

(73) Assignee: Selecto, Inc., Suwanee, GA (US)

( * ) Notice: Subject to any disclaimer, the term of this patent is extended or adjusted under 35 U.S.C. 154(b) by 17 days.

This patent is subject to a terminal disclaimer.

(21) Appl. No.: 11/808,695

(22) Filed: Jun. 12, 2007

(65) Prior Publication Data

US 2007/0241051 A1    Oct. 18, 2007

Related U.S. Application Data

(63) Continuation of application No. 10/445,410, filed on May 27, 2003, now Pat. No. 7,264,726, which is a continuation-in-part of application No. 09/854,010, filed on May 11, 2001, now Pat. No. 6,662,956, which is a continuation-in-part of application No. 09/805,758, filed on Mar. 13, 2001, now Pat. No. 6,630,106, which is a continuation-in-part of application No. 09/772,542, filed on Jan. 30, 2001, now abandoned, and a continuation-in-part of application No. 09/560,824, filed on Apr. 28, 2000, now abandoned, which is a continuation-in-part of application No. 08/819,999, filed on Mar. 18, 1997, now Pat. No. 6,241,893.

(51) Int. Cl.
*B01D 39/14* (2006.01)

(52) U.S. Cl. .................. 210/502.1; 210/504; 210/506; 210/510.1; 264/122; 264/DIG. 48; 502/402; 502/414; 502/417

(58) Field of Classification Search ............... 210/501, 210/503, 504, 506, 502.1, 510.1; 264/122, 264/DIG. 48; 502/402, 417, 400, 414
See application file for complete search history.

(56) References Cited

U.S. PATENT DOCUMENTS

| | | | |
|---|---|---|---|
| 3,420,709 A * | 1/1969 | Barrett, Jr. et al. ...... | 210/502.1 |
| 4,045,553 A | 8/1977 | Mitsumori et al. | |
| 4,061,807 A | 12/1977 | Shaler et al. | |
| 4,144,171 A | 3/1979 | Krause | |
| 4,199,449 A | 4/1980 | Slejiko | |
| 4,336,043 A | 6/1982 | Aonuma et al. | |
| 4,361,486 A | 11/1982 | Hou et al. | |
| 4,504,290 A | 3/1985 | Pontius | |
| 4,569,756 A | 2/1986 | Klein | |
| 4,678,571 A | 7/1987 | Hosaka et al. | |
| 4,753,728 A * | 6/1988 | VanderBilt et al. ......... | 210/506 |
| 4,834,876 A | 5/1989 | Walker | |
| 5,019,311 A | 5/1991 | Koslow | |
| 5,064,534 A | 11/1991 | Bush et al. | |
| 5,133,871 A | 7/1992 | Levy | |
| 5,249,948 A | 10/1993 | Koslow | |
| 5,342,528 A | 8/1994 | Adachi et al. | |
| 5,424,077 A | 6/1995 | Lajoie | |
| 5,443,735 A | 8/1995 | Kirnbauer et al. | |
| 5,458,767 A | 10/1995 | Stone | |
| 5,460,734 A | 10/1995 | Birbara et al. | |
| 5,478,470 A | 12/1995 | Fukuda et al. | |
| 5,538,746 A | 7/1996 | Levy | |
| 5,554,288 A | 9/1996 | Rydell et al. | |
| 5,612,522 A | 3/1997 | Levy | |
| 5,616,243 A | 4/1997 | Levy | |
| 5,632,890 A | 5/1997 | Sugimoto | |
| 5,639,550 A * | 6/1997 | Lisenko ...................... | 210/504 |
| 5,645,727 A | 7/1997 | Bhave et al. | |
| 5,655,212 A | 8/1997 | Sekhar et al. | |
| 5,685,986 A | 11/1997 | Yamada et al. | |
| 5,688,588 A | 11/1997 | Cotton et al. | |
| 5,730,918 A | 3/1998 | Nikolskaja et al. | |
| 5,750,026 A | 5/1998 | Gadkaree et al. | |
| 5,776,353 A | 7/1998 | Palm et al. | |
| 5,855,788 A | 1/1999 | Everhart et al. | |
| 5,900,146 A | 5/1999 | Ballard et al. | |
| 5,985,790 A | 11/1999 | Moskovitz et al. | |
| 5,989,420 A | 11/1999 | Sugimoto | |
| 6,077,436 A | 6/2000 | Rajnik et al. | |
| 6,093,236 A * | 7/2000 | Klabunde et al. ........... | 502/400 |
| 6,093,664 A | 7/2000 | White et al. | |
| 6,103,122 A | 8/2000 | Hou et al. | |
| 6,129,846 A | 10/2000 | Gadkaree | |
| 6,136,189 A | 10/2000 | Smith et al. | |
| 6,171,489 B1 | 1/2001 | Ballard et al. | |
| 6,187,192 B1 | 2/2001 | Johnston et al. | |
| 6,241,893 B1 * | 6/2001 | Levy ........................ | 210/502.1 |
| 6,630,106 B1 * | 10/2003 | Levy ........................ | 210/758 |
| 6,662,956 B2 * | 12/2003 | Levy ........................ | 210/501 |
| 7,264,726 B1 * | 9/2007 | Levy ........................ | 210/502.1 |

FOREIGN PATENT DOCUMENTS

| | | |
|---|---|---|
| EP | 0 515 936 A1 | 12/1992 |
| JP | 06-192961 | 7/1994 |
| JP | 06-315614 A | 11/1994 |
| WO | WO 96/06814 | 3/1996 |
| WO | WO 96/37288 | * 11/1996 |

OTHER PUBLICATIONS

KX Industries Technical Data Bulletin, "The Features and Benefits of Extruded Carbon Filters: Axizl vs. Radial Flow" 1997.*

(Continued)

*Primary Examiner*—Christopher Upton
(74) *Attorney, Agent, or Firm*—Buchann Ingersoll & Rooney PC

(57) ABSTRACT

The invention relates to filtration media having nanocrystals of metal oxides, encapsulated in or impregnated into a binder matrix, which binds together particles of activated carbon. The filtration media can be compressed into a filtration block, has low pressure drop, and has excellent microbial removal properties.

16 Claims, No Drawings

OTHER PUBLICATIONS

James S. Reed, *"Principles of Ceramic Processing,"* pp. 588-594, 2d Ed., 1995.

William D. Callister, Jr., *"Materials Science and Engineering An Introduction,"* p. 437, 2000.

Schaffer, et al. *"The Science and Design of Engineering Materials,"* pp. 335-336, 2nd Ed. 1999.

Hawley's Condensed Chemical Dictionary, p. 521, 1987.

Lewis, RJ, Hawley's Condensed Chemical Dictionary (12th Edition), VanNostrand Reinhold, New York (1993), pp. 1153, "Titanium Dioxide".

Lewis, RJ, Hawley's Condensed Chemical Dictionary (12th Edition), VanNostrand Reinhold, New York (1993), pp. 933 "Polyethylene".

Lewis, RJ, Hawley's Condensed Chemical Dictionary (12th Edition), VanNostrand Reinhold, New York (1993), pp. 727 "Manganese Dioxide".

\* cited by examiner

NANOCRYSTAL-CONTAINING FILTRATION MEDIA

This application is a continuation of U.S. Ser. No. 10/445,410, filed May 27, 2003, now U.S. Pat. No. 7,264,726 which is a continuation-in-part of U.S. Ser. No. 09/854,010, filed May 11, 2001, now U.S. Pat. No. 6,662,956 which is a continuation-in-part of U.S. Ser. No. 09/805,758, filed Mar. 13, 2001, now U.S. Pat. No. 6,630,106 a continuation-in-part of U.S. Ser. No. 09/772,542, filed Jan. 30, 2001, now abandoned, and a continuation-in-part of U.S. Ser. No. 09/560,824, filed Apr. 28, 2000, now abandoned, which is a continuation-in-part of U.S. Ser. No. 08/819,999, filed Mar. 18, 1997, now U.S. Pat. No. 6,241,893, the entire contents of each of which are hereby incorporated by reference.

BACKGROUND OF THE INVENTION

1. Field of the Invention

The invention relates to a filtration media containing nanocrystals made of metal oxide dispersed in a binder matrix for the removal of microorganisms and other contaminants from water.

2. Description of Related Art

Drinking water, in some locations world-wide, contains bacteria and viruses that are harmful to humans, in many cases, rendering the water unfit for consumption. There are a variety of different techniques and equipment that can reduce bacteria and viruses to certain acceptable performance levels, such as ceramic filters, sub-micron filters, ion exchange resins, ultra-violet lights, ozonators, distillation equipment, and other apparatus. Microfiltration generally presents significant drawbacks because of the large pressure drops involved and because of the limited capacity of the microfilters. With bacteria having sizes of around 0.1 micron, such as *B. diminuta*, the performance of microfilters is generally very poor, and clogging takes place in a short time. Consumers who use these filters to reduce bacteria generally must rely on increased pressure drop as the only indication that it is time to replace the microfilter. There is no reliable method to determine whether the filter will last 10, 50, 100 or 1000 gallons, or what the remaining capacity of a filter in use might be. Turbidity and the presence of other contaminants than microorganisms can affect the surface of the microfilter, which creates some limitations on the use of the filter. Ultra-violet lights are affected by scale buildup on the lamp sites and frequency changes that may affect their performance in bacteria reduction, and UV wavelength sensors are very expensive.

Filtration media are often assigned a "rating" based upon the size of particulates that can be removed from water using these filters. Typical testing to establish these ratings includes NSF Class 1 Particulate and NSF 53 AC Dust testing. Reducing the ratings (desirable, because it indicates that smaller particles can be produced) generally requires the use of specialized particles having very small pore sizes. These particles become difficult and expensive to produce, so that decreasing the nominal rating of the filtration media is limited by the expense of the particles necessary to include in the media. In addition, filters that have submicron ratings, and which function by occlusion, have very short lifetimes. For example, a 0.2 micron rated filter of approximately 3 in. diameter and 10 in. length filtering New York City water at 1 gpm will suffer reduced capacity and significantly increased pressure drop after filtering only 100 gallons of water.

Recent advances in "hybrid" materials, i.e., nanostructured materials that contain both organic and inorganic components or moieties, has led to the development of filtration materials capable of achieving submicron level removal of particulates as well as removal of microorganisms, but that are capable of operating at high flow rates and for extended periods of time without substantial degradation of performance. The invention described herein is one such material.

SUMMARY OF THE INVENTION

It has been found that combining nanocrystals of metal oxides, such as zinc oxide or titanium oxide or mixtures thereof, encapsulated in or impregnated into a binder matrix. The binder matrix may be a polymeric material, and the metal oxide nanocrystals may be optionally mixed with carbon and/or other organic particulates. The inclusion of the metal oxide nanoparticles significantly decreased the micron rating of the filtration material as compared to the same material without the nanoparticles, and provided a material that is capable of reducing levels of microorganisms, such as bacteria, including those having an average particle size ranging from about 0.1 to about 1 micron, at an efficiency of 99.999% in water, and in particular, in water used for human and animal consumption.

Without wishing to be bound by any theory, it is believed that the filtration media functions to remove microorganisms without significant size exclusion of the microorganisms. Regardless of the exact mechanism by which the material functions, it allows the preparation of a filtration media that is capable of removing submicron contaminants at extremely high efficiency. The inclusion of metal oxide nanoparticles in the filtration media allows the use of binder and, e.g., carbon particulates suitable for achieving a micron or larger nominal rating, but in fact achieving submicron performance without diminished lifetime. By contrast with the 0.2 micron filter described above, a similar filter including metal oxide nanoparticles can process over 1000 gallons of the same water at the same flow rate with less than a 30% pressure drop at the end of processing.

DETAILED DESCRIPTION OF SPECIFIC EMBODIMENTS

According to the invention, nanocrystals of metal oxides having particles sizes ranging from approximately 20 nm to 400 nm are incorporated into a filtration media containing a binder matrix. Desirably, this filtration media also contains some form of additional particulate, such as activated carbon, and the binder is desirably a polymeric material. The resulting filtration media is capable of destroying bacteria and other organisms having sizes below 1 micron.

The filtration media of the invention can be viewed as a microcoating of metal oxide nanocrystals on the surface of a polymeric binder (including internal surfaces, such as those provided by pores within the binder matrix). The metal oxide nanocrystals are included in amounts ranging from approximately 0.1% up to about 10% by weight, based upon the weight of the entire filtration media. Suitable metal oxides include, but are not limited to, zinc oxide, copper oxide, aluminum oxide, and titanium dioxide. For example, 1% $Al_2O_3$, based on the total weight of the filtration composition, provides good performance. Other metal oxide nanocrystals may also be suitable, and this can be determined by preparing suitable filter blocks containing these metal oxide nanocrystals, as described herein, and testing the blocks against submicron particles and against microorganisms, as described herein, to determine their suitability.

The nanocrystals are believed to interact with the binder, which is typically a polymeric binder, such as high-density polyethylene or low-density polyethylene or a mixture thereof. The nanocrystals are typically combined with the polymer and, before or after the addition of other optional components such as activated carbon, heated to a temperature ranging from about 150° C. to about 250° C. The nanocrystals can be incorporated into the polymer by, e.g., high-speed shear mixing for approximately 10-30 minutes in the mixer. The nanocrystals and the polymeric binder in particulate form, wherein the binder particles typically have a particle size ranging from about 5 to about 160 µm, are simply added to the mixer in the requisite quantities, and mixed. Activated carbon and optionally zirconia can then be added. The binder particle size has been found to be important in allowing the preparation of filters having large porosities, and/or having relatively large sized particles of activated carbon.

The order of addition is not critical, however it is generally desirable to add the nanocrystals to the binder prior to adding other components and prior to heating, in order to assure complete mixing. The resulting mixture is then heated to raise the temperature of the polymeric binder, typically to a temperature between about 150° F. and about 500° F., depending on the particular binder used. In general, the polymeric binder material containing the metal oxide nanocrystals is heated slowly to form the filtration media. For example, polymeric binders containing the metal oxide nanocrystals and HDPE binders are then heated from about 30 minutes to about 6 hours at an approximate temperature of 550° F. in order to form a block of filtration media. The mixture can desirably be compressed at a pressure of about 60 psi to about 100 psi during, or desirably, after this heating step to provide formation of the desired block shape. After heating, the resulting material is cooled to ambient temperature.

In an alternative embodiment, the material can be mixed and heated to at or near the melting temperature of the polymeric binder material, and the mixture extruded through a die having the desired cross-sectional shape, and cooled to form the desired filtration block. In this embodiment, the extrusion can supply part or all of the heat needed to sufficiently soften the binder material, and the extruder can supply the pressure needed to sufficiently compact the mixture.

In compositions containing both metal oxide nanoparticles and carbon black, the binder can be present in amounts ranging between about 10% and about 25%, more particularly from about 12% to about 20% by weight, based on the total weight of the composition. Suitable binders include polyolefins, such as polyethylene homopolymers, acrylic resins, nylons, carboxymethylcelluloses, polyvinyl acetates, and the like, as well as blends and copolymers thereof. In particular, when polyethylene homopolymers, blends, or copolymers are used, they may include those known in the art as "high molecular weight" polyethylenes and those known as "low molecular weight" polyethylenes.

In general, activated carbon particles ranging in size between about 30 µm and about 500 µm are suitable for use in the filtration media of the invention. A number of different sizes of activated carbon were used with positive effect against both E. coli and cysts. The particle size ranges for these carbons is given below:

| PARTICLE SIZE RANGE | PERCENT IN RANGE |
|---|---|
| 30-300 µm | 90 |
| 75-300 µm | 86 |
| 50-400 µm | 94 |
| 50-460 µm | 87 |
| 106-180 µm | 99 |

PREPARATION EXAMPLE

High-density polyethylene particles, in amounts ranging from 15-20 wt %, based on the total mixture, are combined with 2 wt % ZnO nanocrystals having particle sizes in the range of about 20 nm to about 100 nm, which have been prepared by plasma vaporization, quenching, and cooling (i.e., by a "fuming" process), with 7 wt % particulate zirconia, and with the balance particulate active carbon. The mixture is filled into a round cylindrical metal alloy mold designed to evenly distribute heat across its surface. The material is then compressed to 100 psi under heating at temperatures ranging from about 300° F. to about 500° F. for at least about 1 hour, up to a maximum of about 6 hours. After compression, the material is then cooled to ambient temperature. The resulting block of material can then be used as a filtration media that will reduce the level of microorganisms in a fluid.

It has been found that quantities of titanium dioxide nanocrystals as low as 7.5 micrograms demonstrated the capacity to repeatedly (over 56 times) destroy E. coli colonies in water (30,000 counts in 1000 cc of water). An average sized filter prepared from the filtration media of the invention contains around 0.5% by weight, based on the total weight of the filtration media, of nanocrystals of zirconia or titania or both, and is capable of destroying tens of billions of bacteria. The percentage of metal oxide nanocrystals impregnated into the polymer can determine the capacity of the filter for the reduction of bacteria and other microorganisms. For instance, passing approximately 400 gallons of water containing B. diminuta at a concentration of 10,000 ct/cc at a flow rate of 0.5 to 1 gpm through a 2.5 in. diameter×10 in. cylindrical filter with a nominal micron rating of approximately 1-5 micron and having around 0.5 wt % nanocrystals of titania or zinc oxide or mixtures thereof (based on the total weight of the filtration media) can reduce the bacteria count by 99.999%. This same filter can achieve the same efficiency with water containing 1,000 ct/cc over the course of treating approximately 1,500 gallons of water at similar flow rates. Since the average toxic bacteria count in water under the worst expected conditions would typically not exceed 1,000-3,000 ct/cc in drinking water (which is considered unacceptable for human consumption), the nanocrystals combined with zirconia can be calculated accurately for the capacity of the filter of a given size with a given flow rate.

In addition, it has been found that incorporation of the nanocrystals improves the performance of the polymer-carbon filtration media tremendously, possibly by controlling the complexing of the binder, and/or improving the surface structure of the carbon, polymeric binder, and metal oxide combination. Testing was conducted using a filtration media produced by compressing coarse carbon having an average particle size of approximately 50-100 microns, polymer binder particles having an average particle size of approximately 30 microns, with and without 0.2% of nanocrystalline titanium oxide. When the nanocrystalline titanium oxide was included, a 99.999% efficiency one-micron filter was obtained. Without the nanocrystalline titanium oxide, the rating of the filter was approximately 5-20 microns, more particularly 10 micron. The inclusion of 0.5% of nanocrystalline titanium oxide results in the ability to form a one-micron filter (i.e., a filter capable of removing 1 micron particle dust in test water at a level of 50,000 ct/cc with an efficiency of 99.99%).

The 0.1 wt % nanocrystalline titanium oxide filter described above was tested by NSF for bacteria reduction.

EXAMPLE 1

5000 gallons of water seeded with 30,000 ct/cc *E. coli* were passed through a 169 cu. in. filter having a micron rating of 2, at 3 gpm, with an inlet pressure of 60 psi and an outlet pressure of 52 psi. The filter compositions were 0.5% nanocrystalline titanium oxide, 6% zirconia crystals, 20% high density HDPE and the balance activated carbon. The filtration media resulted in a bacterial reduction efficiency of 99.9999%.

EXAMPLE 2

The test described above in Example 1 was also conducted by seeding the water with 0.1-micron bacteria (*B. diminuta*) at a concentration of approximately 70,000 ct/cc, and using 4,000 gallons of water. The filtration media demonstrated a bacterial reduction efficiency of 99.999%.

The filtration media used in the above examples can theoretically purify 30,000 gallons or more of water if the incoming count of bacteria does not exceed about 2,000 ct/cc.

COMPARATIVE EXAMPLE 1

A ceramic filter block having a 0.2 micron rating, in the form of a cylindrical block of diameter 2½ inches and a length of 20 inches was tested for reduction of *E. coli* and *B. diminuta* by passing water through the filtration block at a variable flow rate as indicated below.

| Flow at: | 15 min. | 1.3 gpm |
|---|---|---|
| | 60 min. | 0.2 gpm |
| | 90 min. | 0.1 gpm |
| | Total flow | 102 gallons |

The level of *E. coli* bacteria in the test water was 70000 ct/cc; the total of the dissolved solids of the water was 300 ppm, and the hardness of the water was 200 ppm. The ceramic filter reduced *E. coli* at an efficiency of 99.9% at the beginning of the experiment, and at an efficiency of 99.99% at the end of the experiment.

The level of *B. diminuta* in the test water was 60,000 ct/cc, and the flow rate was varied as indicated below:

| Flow at: | 1 min. | 1.6 gpm |
|---|---|---|
| | 2 min. | 0.4 gpm |

The total dissolved solids content and hardness of the water are as indicated above with respect to testing for *E. coli*.

The reduction after 90 min. was 92%.

EXAMPLE 3

A cylindrical block filtration media was prepared by mixing 2 wt % ZnO nanocrystals with 20 wt % high-density polyethylene binder, 7 wt % zirconia and 71 wt % activated carbon, and heating this mixture under pressure to form a block having a diameter of 3½ inches and a length of 20 inches. The filter was tested for *E. coli* and *B. diminuta* removal efficiency as indicated below:

| *E. coli* bacteria reduction: 70,000 ct/cc | | |
|---|---|---|
| Flow at: | 1 min. | 3 gpm |
| | 5000 gallons: | 3 gpm |
| Reduction: | | 99.999% |
| *B. diminuta* bacteria reduction: 70,000 ct/cc | | |
| Flow at: | 1 min. | 3 gpm |
| | 3,000 gallons: | 3 gpm |
| Reduction at 3,000 gallons: | | 99.999% |

These examples demonstrate that the use of nanocrystalline titanium oxide allows the preparation of a polymeric binder-based filtration media having an exact micron rating filter with 99.99% accuracy, and much lower than is possible using the polymeric binder without the nanocrystalline particles. Most manufacturers of carbon block filters add approximately 5% carbon dust, or zeolite, or clay particles, or mixtures of these, having average particle sizes of about 32 microns to improve the filtration capabilities to obtain a 1 micron rating (i.e., an efficiency at removing 1 micron particles of 99.99%). In most cases, 5% carbon dust is very difficult to control on the surface of the binder, and substantial added amounts of pressure are required to get a uniform product. The filter block containing nanocrystals has been found to work well under compression, from as low as 30 psi to as high as 500 psi. The performance of the surface of the nanocrystals is not affected by the pressure, or by the heat.

What is claimed is:

1. A filtration media for water, comprising:
   a cylindrical block filtration media, comprising:
      a polymeric binder matrix;
      a plurality of metal oxide nanoparticles, selected from the group consisting of titanium oxide zinc oxide, aluminum oxide, zirconium oxide, and mixtures thereof, dispersed and encapsulated in the polymeric binder, and
      a plurality of activated carbon particles bound together by the polymeric binder.

2. The filtration media of claim 1, wherein the nanoparticles are present in an amount ranging from about 0.1 wt % to about 10 wt %, based upon the total weight of the filtration media.

3. The filtration media of claim 2, wherein the nanoparticles are present in an amount of about 0.5 wt %, based on the total weight of the filtration media.

4. The filtration media of claim 1, wherein the nanoparticles have an average particle size ranging from about 20 nm to about 1000 nm.

5. The filtration media of claim 1, wherein the activated carbon particles have particle sizes ranging between about 30 μm and about 500 μm.

6. The filtration media of claim 5, wherein the activated carbon particles have particle sizes ranging between about 30 μm and about 200 μm.

7. The filtration media of claim 1, wherein the polymeric binder is selected from the group consisting of polyolefins, acrylic resins, nylons, carboxymethylcelluloses, polyvinyl acetates, and blends and copolymers thereof.

8. The filtration media of claim 7, wherein the polymeric binder is a high-density polyethylene.

9. The filtration media of claim 1, wherein the weight ratio of nanoparticles to polymeric binder ranges between about 30:1 and about 5:1.

10. The filtration media of claim 9, wherein the weight ratio of nanoparticles to polymeric binder ranges between about 20:1 and about 10:1.

11. A method of making a filtration media for water, wherein said filtration media comprises a cylindrical block filtration media, comprising: a polymeric binder matrix; a plurality of metal oxide nanoparticles, selected from the group consisting of titanium oxide zinc oxide, aluminum oxide, zirconium oxide, and mixtures thereof, dispersed and encapsulated in the polymeric binder, and a plurality of activated carbon particles bound together by the polymeric binder, comprising:
   combining about 0.1 wt % to about 10 wt % metal oxide nanoparticles with about 10 wt % to about 25 wt % particles of polymeric binder and the balance particles of activated carbon;
   heating the mixture to a temperature above the melting temperature of the polymeric binder;
   compressing the heated mixture at said temperature for a period of time sufficient to allow formation of the cylindrical block filtration media; and
   cooling the cylindrical block filtration media to ambient temperature.

12. The method of claim 11, wherein the metal oxide nanoparticles have particle sizes ranging from about 10 nm to about 1000 nm.

13. The method of claim 11, wherein the polymeric binder particles have particle sizes ranging from about 5 µm to about 60 µm.

14. The method of claim 11, wherein the activated carbon particles have particle sizes ranging between about 30 µm and about 500 µm.

15. The method of claim 11, wherein said combining comprises first mixing the metal oxide nanoparticles and polymeric binder particles using rapid shear mixing, followed by addition of activated carbon particles and additional mixing.

16. A method of making a filtration media for water, wherein said filtration media comprises a cylindrical block filtration media, comprising: a polymeric binder matrix; a plurality of metal oxide nanoparticles, selected from the group consisting of titanium oxide zinc oxide, aluminum oxide, zirconium oxide, and mixtures thereof, dispersed and encapsulated in the polymeric binder, and a plurality of activated carbon particles bound together by the polymeric binder, comprising:
   combining about 0.1 wt % to about 10 wt % metal oxide nanoparticles with about 10 wt % to about 25 wt % particles of polymeric binder and the balance particles of activated carbon;
   extruding the mixture into a cylindrical block filtration media; and
   cooling the cylindrical block filtration media to ambient temperature.

* * * * *